US00PP09699P

United States Patent [19]

VandenBerg

[11] Patent Number: Plant 9,699

[45] Date of Patent: Nov. 19, 1996

[54] CHRYSANTHEMUM PLANT NAMED 'SARASOTA'

[75] Inventor: Cornelis P. VandenBerg, Salinas, Calif.

[73] Assignee: Yoder Brothers, Inc., Barberton, Ohio

[21] Appl. No.: 544,099

[22] Filed: Oct. 17, 1995

[51] Int. Cl.[6] ..... A01H 5/00

[52] U.S. Cl. ..... Plt./74.1

[58] Field of Search ..... Plt./74.1, 76, 82.4

*Primary Examiner*—Howard J. Locker

*Attorney, Agent, or Firm*—Foley & Lardner

[57] ABSTRACT

A Chrysanthemum plant named Sarasota particularly characterized by its flat capitulum form; anemone capitulum type; light red-purple ray floret color with a dark red-purple anemone cushion; diameter across face of capitulum of 57 to 64 mm when fully opened, when grown as a single stem spray cut mum; flowering response is 52 to 58 days after start of short days; plant height is 71 to 81 cm when grown with 18 long days prior to start of short days; peduncle length of the first lateral at flowering after removing the apical bud is 5 to 8 cm; peduncle length of the fourth lateral at flowering is 8 to 13 cm; and recommended as a spray cut mum.

3 Drawing Sheets

The present invention comprises a new and distinct cultivar of Chrysanthemum, botanically known as *Dendranthema grandiflora,* and referred to by the cultivar name Sarasota.

Sarasota, identified as B684 (92-929002), was originated from a cross made by Cornelis P. VandenBerg in a controlled breeding program in Salinas, Calif., in 1991.

The female parent of Sarasota was an unnamed seedling, identified as 3606 (89-#02024), and described as an anemone spray cut mum, with a light pink ray floret color and a dark red anemone cushion. The female parent of Sarasota was discarded from all programs in September 1991.

The male parent of Sarasota was an unnamed seedling, identified as 2331 (88-032004) and described as an anemone spray cut mum with a white ray floret color and white anemone cushion. The male parent of Sarasota was discarded from all programs in May 1995.

Sarasota was discovered and selected as one flowering plant within the progeny of the stated cross by Cornelis P. VandenBerg in January 1993, in a controlled environment in Salinas, Calif.

The first act of asexual reproduction of Sarasota was accomplished when vegetative cuttings were taken from the initial selection in March 1993 in a controlled environment in Salinas, Calif., by technicians working under supervision of Cornelis P. VandenBerg.

Horticultural examination of controlled flowerings of successive plantings has shown that the unique combination of characteristics as herein disclosed for Sarasota are firmly fixed and are retained through successive generations of asexual reproduction.

Sarasota has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Sarasota, which, in combination, distinguish this Chrysantheum as a new and distinct cultivar.

1. Flat capitulum form.
2. Anemone capitulum type.
3. Light red-purple ray floret color with a dark red-purple anemone cushion.
4. Diameter across face of capitulum of 57 to 64 mm when fully opened, when grown as a single stem spray cut mum.

5. Flowering response is 52 to 58 days after start of short days.
6. Plant height is 71 to 81 cm when grown with 18 long days prior to start of short days.
7. Peduncle length of the first lateral at flowering after removing the apical bud is 5 to 8 cm. Peduncle length of the fourth lateral at flowering is 8 to 13 cm.
8. Recommended as a spray cut mum.

The accompanying photographic drawings show typical inflorescence and leaf characteristics of Sarasota, with the colors being as nearly true as possible with illustrations of this type.

Sheet 1 is a color photograph of Sarasota grown as a single stem spray cut mum, grown in Salinas, Calif.

Sheet 2 is a black and white photograph of three views of the inflorescence of Sarasota.

Sheet 3 is a black and white photograph showing the upper and under sides of the leaves of Sarasota at 3 stages of development (mature, intermediate and immature). In sheets 2 and 3 a measuring tape in centimeters has been added.

Of the commercial cultivars known to the inventor, the most similar in comparison to Sarasota is the cultivar identified as Funshine, disclosed in U.S. Pat. No. P.P. 8,106. Reference is made to attached Chart A, which compares certain characteristics of Sarasota with the same characteristics of Funshine. Similar traits are ray floret color, capitulum form and type, and peduncle length. Plant height of Sarasota and Funshine is comparable. Sarasota has a dark red-purple anemone cushion, while Funshine has a dark red anemone cushion. Sarasota has a large diameter of capitulum and a slower flowering response to short days than Funshine.

In the following description color references are made to The Royal Horticultural Society Colour Chart. The color values were determined on plant material grown as a single stem spray cut mum in Salinas, Calif. on Jul. 7, 1995.

Classification:

*Botanical.*—*Dendranthema grandiflora* cv. Sarasota.

*Commercial.*—Flat anemone spray cut mum.

INFLORESCENCE

A. Capitulum:

*Form.*—Flat.

*Type.*—Anemone.

*Diameter across face.*—57 to 64 mm when fully opened.

B. Corolla of ray florets:

*Color* (*general tonality from a distance of three meters*).—Light red-purple with dark red-purple anemone cushion.

*Color* (*upper surface*).—White, tinged with 65D.

*Color* (*under surface*).—White, tinged with 65D.

*Shape.*—Straight, cross section concave, rounded petal tip.

C. Corolla of disc florets:

*Color anemone cushion* (*mature*).—65C to 65D.

*Color anemone cushion* (*immature*).—60B to 60C.

D. Reproductive organs:

*Androecium.*—Present on disc florets only; scant to moderate pollen.

*Gynoecium.*—Present on both ray and disc florets.

PLANT

A. General appearance:

*Height.*—71 to 81 cm when grown in Salinas with 18 long days prior to start of short days.

B. Foliage:

*Color* (*upper surface*).—147A.

*Color* (*under surface*).—147B.

*Shape.*—Deeply lobed, strongly serrated.

CHART A

COMPARISON OF SARASOTA AND FUNSHINE

| CHARACTERISTIC | SARASOTA | FUNSHINE |
|---|---|---|
| Ray floret color | White, tinged with light red-purple | White, tinged with light red-purple |
| Color anemone cushion | Dark red-purple | Dark red |
| Capitulum form | Flat | Flat |
| Capitulum type | Anemone | Anemone |
| Diameter across face of capitulum | 57 to 64 mm | 38 to 44 mm |
| Flowering response | 52 to 58 days | 49 to 56 days |
| Plant height | 71 to 81 cm | 74 to 81 cm |
| Peduncle length | | |
| 1st lateral | 5 to 8 cm | 5 to 8 cm |
| 4th lateral | 8 to 13 cm | 8 to 13 cm |

COMPARISONS MADE OF PLANTS GROWN AS SINGLE STEM SPRAY CUT MUMS IN SALINAS, CALIFORNIA

What is claimed is:

1. A new and distinct Chrysanthemum plant named Sarasota, as described and illustrated.

* * * * *

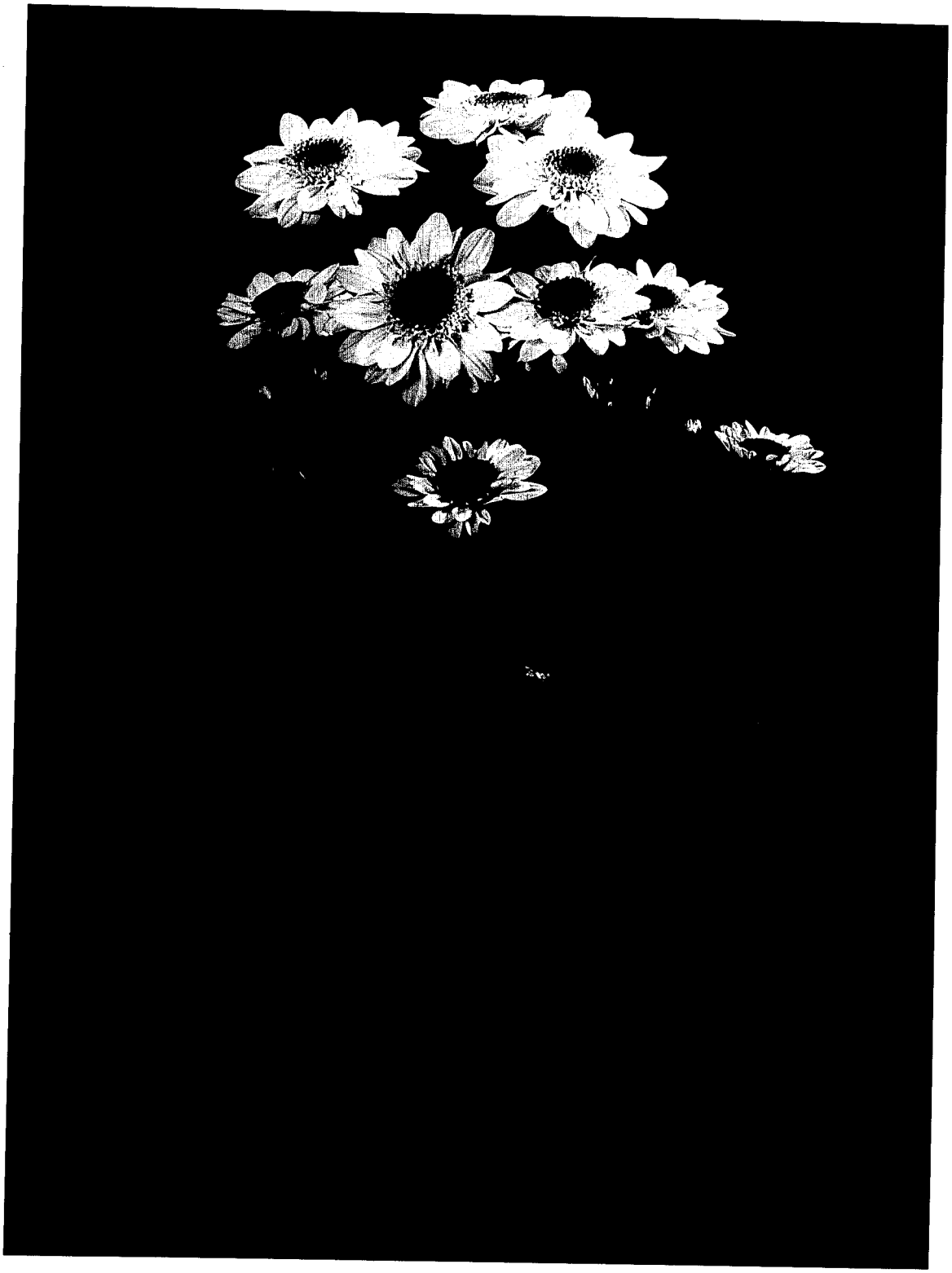

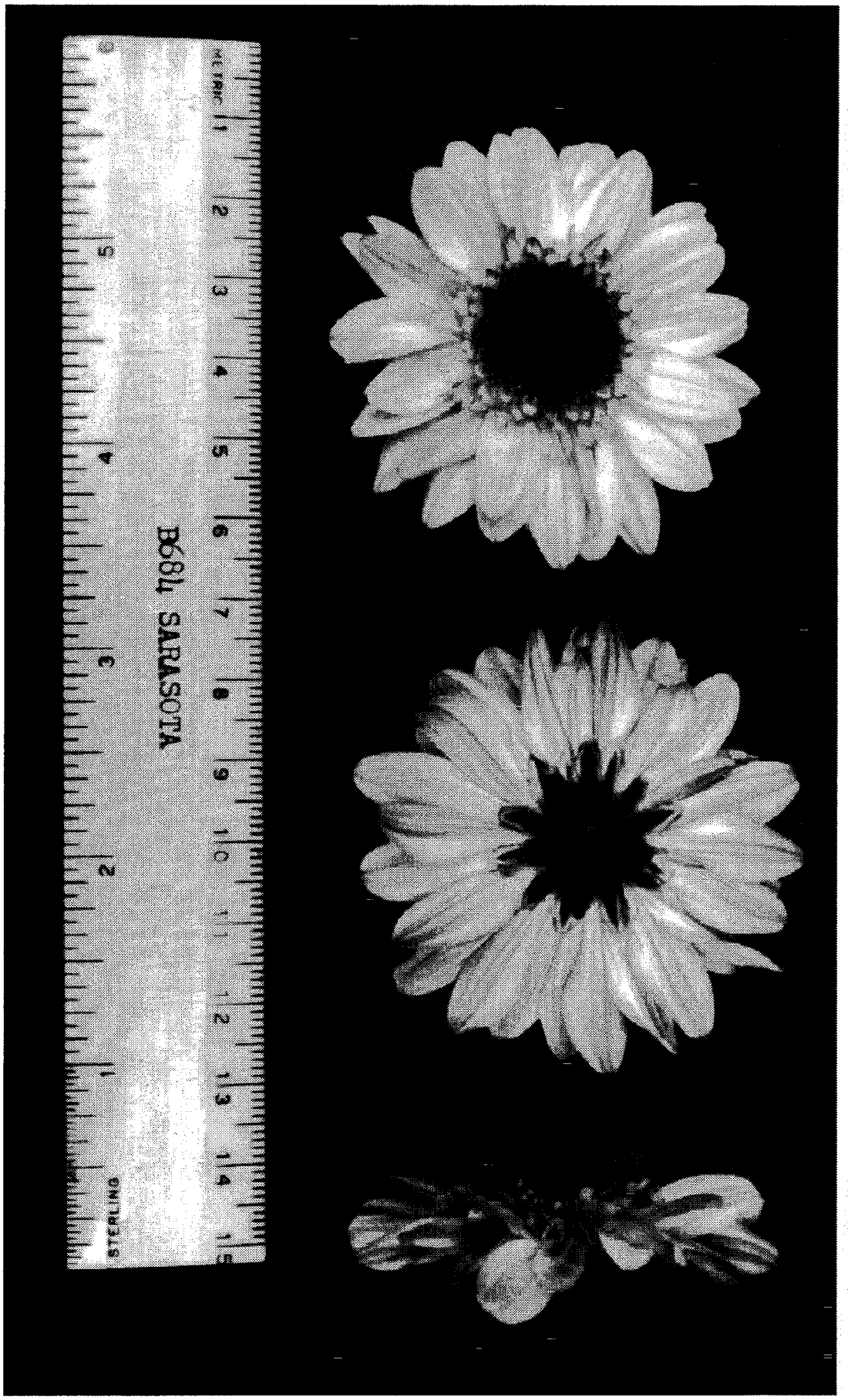
B684 SARASOTA
STERLING

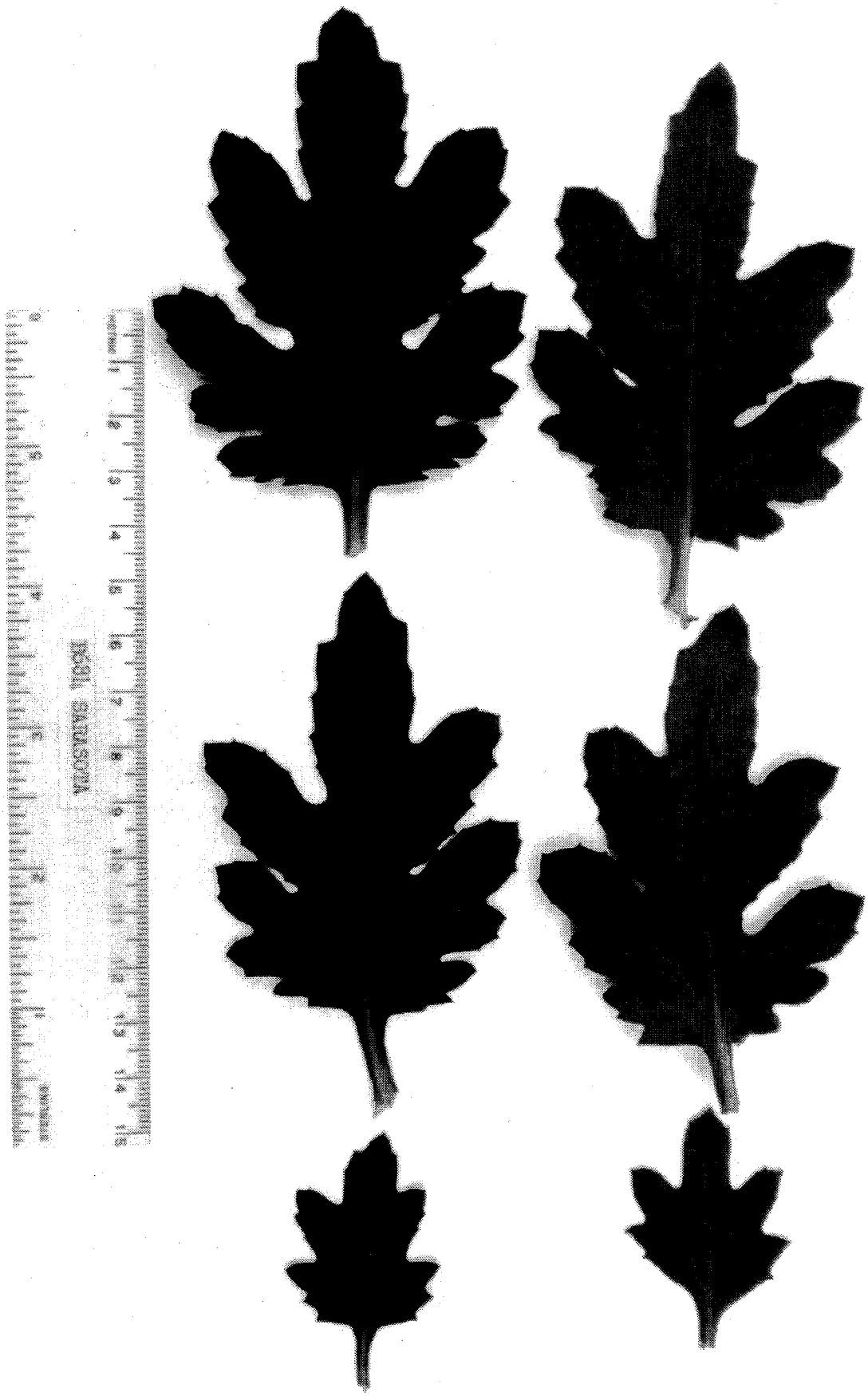
SCALE EXAMPLE